Figure 1:
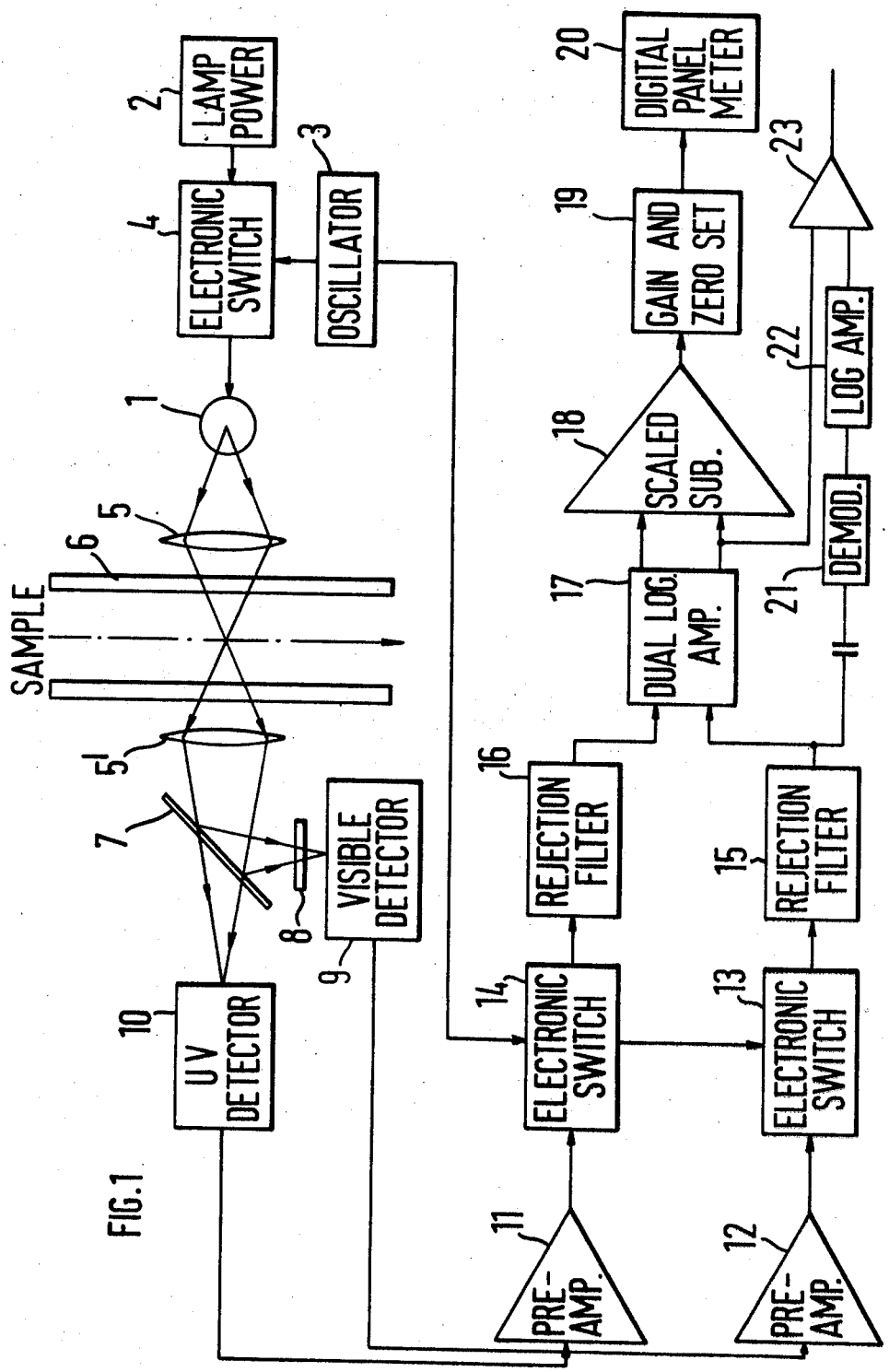

United States Patent [19]

Briggs

[11] 4,077,724

[45] Mar. 7, 1978

[54] OPTICAL DENSITY MEASUREMENT

[75] Inventor: Ronald Briggs, Knebworth, England

[73] Assignee: National Research Development Corporation, London, England

[21] Appl. No.: 627,452

[22] Filed: Oct. 30, 1975

Related U.S. Application Data

[63] Continuation of Ser. No. 438,275, Jan. 31, 1974, abandoned.

[30] Foreign Application Priority Data

Feb. 9, 1973 United Kingdom ............... 6598/73

[51] Int. Cl.² ........................................... G01N 21/06
[52] U.S. Cl. .................................... 356/208; 250/564
[58] Field of Search ............... 356/208, 103, 104, 207, 356/208; 250/564

[56] References Cited

U.S. PATENT DOCUMENTS

| 3,413,464 | 11/1968 | Kamentsky | 250/373 |
|---|---|---|---|
| 3,652,850 | 3/1972 | Briggs | 250/373 |
| 3,783,284 | 1/1974 | McCormack | 250/339 |
| 3,879,129 | 4/1975 | Inoue | 356/102 |

OTHER PUBLICATIONS

Glasser et al.; "Simple Photoelectric Process-Stream Analyzer", The Review of Scientific Instruments, vol. 33, No. 10, (Oct. 1962), pp. 1062–1066.

Primary Examiner—Paul A. Sacher
Assistant Examiner—R. A. Rosenberger
Attorney, Agent, or Firm—Cushman, Darby & Cushman

[57] ABSTRACT

The invention concerns a device for the measurement of organic matter in liquid samples. Modulated light is passed through the sample, and the ultraviolet and visible components of the light passing through the sample separated and caused to fall on individual photodetectors. After amplification and demodulation the outputs of the photodetectors are logarithmically amplified and subtracted to obtain the ratio between the two signals.

2 Claims, 2 Drawing Figures

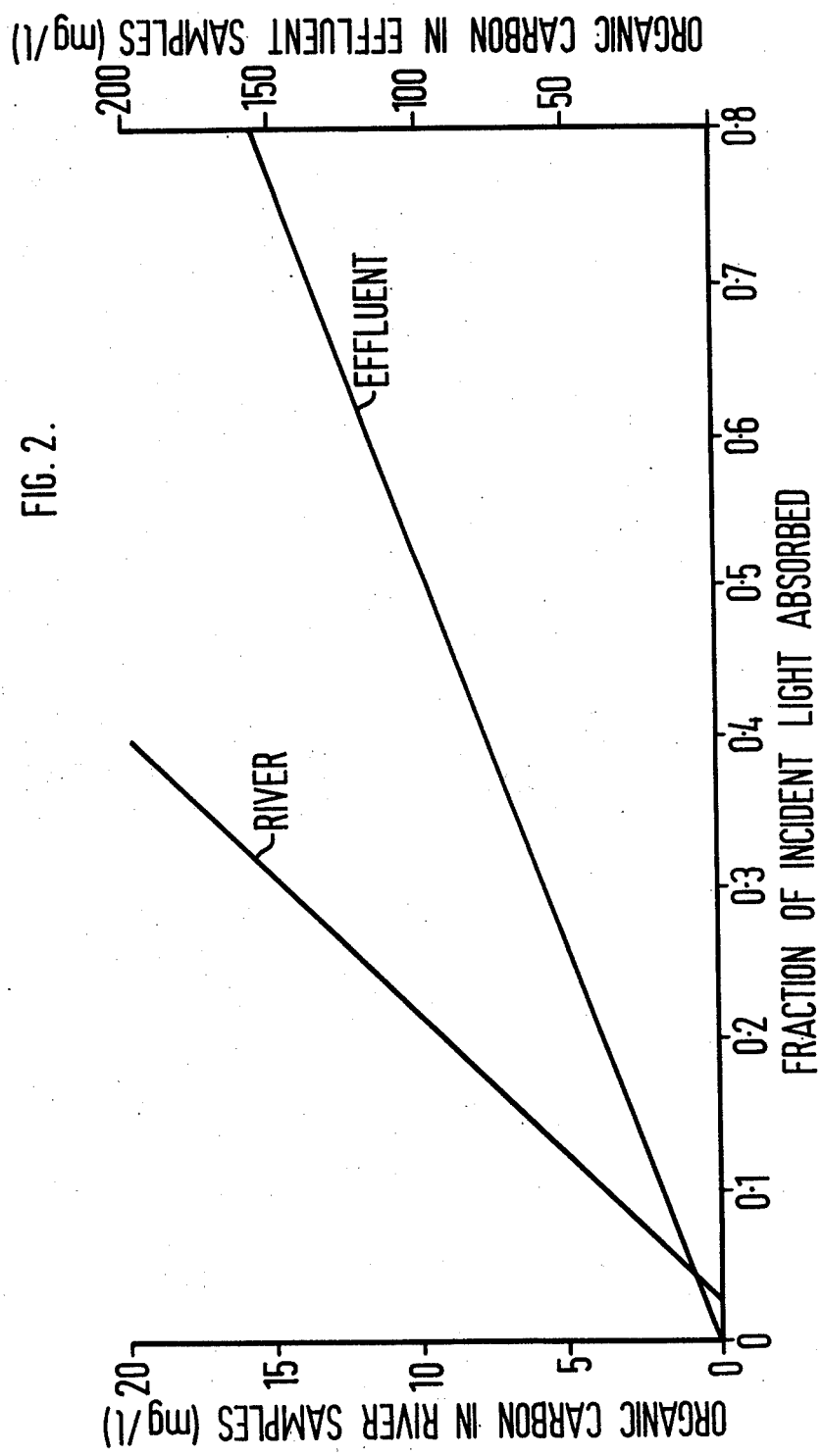

OPTICAL DENSITY MEASUREMENT

This is a continatuion of application Ser. No. 438,275, filed Jan. 31, 1974, now abandoned.

The present invention concerns a device for monitoring organic matter content in water.

One of the more important unsatisfied needs in water quality monitoring is for an instrument for the continuous recording of organic matter.

In accordance with the present invention there is provided a device for measuring the organic matter content of a sample liquid comprising a light source for directing a beam of light through the sample, a pair of photoelectric detectors, one arranged to detect the ultraviolet component of the light transmitted through the sample and the other the visible component, means for logarithmically amplifying the outputs of the two detectors, and means for obtaining the ratio between said logarithmically amplified signals.

Preferably the light transmitted through the sample falls on a dichroic mirror arranged to transmit ultraviolet light and to reflect visible light.

The present invention is based on the observation that the absorption of ultraviolet at an appropriate wavelength can be correlated empirically with the organic carbon content for, for example, both river waters and effluents.

An embodiment of the present invention will now be described by way of example and with reference to the accompanying drawings, in which FIG. 1 is a block diagram of an organic pollution monitor constructed in accordance with the present invention, and FIG. 2 is a graph showing the relationship between the absorption of light at 2537 A and the organic carbon content of samples from six different rivers and three different effluents.

The device shown in the drawing comprises a mercury lamp 1 having a power supply 2. An oscillator 3 drives an electronic switch 4 so that the output of the lamp 1 is modulated to counteract the effect of ambient light. A lens system 5, 5' directs the modulated light through a sample tube 6 of quartz through which fluid the organic content of which is to be monitored is caused to flow. The light after attenuation by the fluid falls on a dichroic mirror 7 which reflects visible light via a visible filter 8 on to a detector 9 whilst ultraviolet light passes through the mirror and falls on an ultraviolet detector 10, thus giving rise to a pair of electrical signals. These signals are amplified in preamplifiers 11, 12 respectively and are supplied via electronic switches 13, 14 controlled in synchronism by the oscillator 3 to a pair of rejection filters 15, 16 tuned to the oscillator frequency and impedance matched. The outputs of the filters are connected to a dual logarithmic amplifier 17. The logarithmically amplified signals are then taken to a scaled subtractor 18 where the two signals are subtracted and thence via a gain and zero setting stage 19 to a digital panel meter 20, on which the organic content of the sample is measured.

The mathematical justification of this circuit is as follows:

If $I_{uv}$ = UV output of lamp
$I_{vis}$ = visible output of lamp
$V_{uv}$ = output of UV detector
$V_{vis}$ = output of visible light decoder
L = path length through water
Ac = light attenuation due to organic matter
As = light attenuation due to suspended solids C and K are constants then $\dfrac{V_{uv}}{V_{vis}} = \dfrac{C \cdot I_{uv} e^{-L(Ac+As)}}{I_{vis} e^{-LAs}} = Ke^{-LAc}$ so that $\ln \dfrac{V_{uv}}{V_{vis}} = \ln K - LAc$ where $K = C \cdot \dfrac{I_{uv}}{I_{vis}}$ Thus the logarithmically amplified output of rejection filter 15 corresponds to Vvis and of filter 16 to Vuv so that the effect of scaled subtractor 18 is the ratio of these two signals and provides the lefthand side of equation (1). In the righthand side of equation (1) K is a constant and L the path length is also constant so that the output of the scaled subtractor 18 is a direct measurement of the organic matter content of the sample.

Also included in the circuit of FIG. 1 is circuitry giving a read out of the amount of solid suspended matter in the sample. The output signal from both of the detectors 9 and 10 will contain a signal in the frequency range 3Hz to 1KHz the amplitude of which will increase logarithmically with the increasing concentrations of solid suspended matter provided that the organic matter content remains constant. This signal can be considered as noise generated by the turbulent solid suspended matter. Thus if this noise signal can be extracted and suitably ratioed against the effective DC level of the original signal a direct measurement of the suspended solid content of the sample can be made. In the present embodiment this is done by taking the output of the rejection filter 15 and demodulating it in a demodulator 21. The demodulated signal is then logarithmically amplified in a logarithmic amplifier 22 and fed into one input of a scaled subtractor 23 the other input of which is taken from the visible signal output of the dual logarithmic amplifier 17. The resultant signal can then be taken via a gain and zero setting stage which is not shown and displayed on a suitable meter.

One of the main difficulties in using an optical system of the kind described is the fouling of the optical surfaces and variations in light output. In the present instrument these difficulties have been largely overcome by recording the ratio of the absorbance in the ultraviolet to that in the visible. This also compensates for errors due to the presence of suspended matter in the sample. This compensation is dependent on the fact that K given the previous equations remains constant for all forms of fouling. However should the compensation be insufficient because of conditions which give rise to rapid and extensive fouling then it is a relatively simple matter to provide an automatic cleaning device in the instrument. Thus the sample tube could be provided with a movable piston having a ceiling link engaging the inner walls of the sample tube. The piston could be attached to a plunger which when required is reciprocated in the tube either manually or by an eccentric. Alternatively the piston could be freely mounted within the ceiling tube which would then be provided with control valves so that the sample fluids could be caused to flow in either direction through the tube. Thus by alternating the direction of flow of the fluid through the tube the piston could be made to reciprocate within the tube, for example at daily intervals thus cleaning the inner surfaces of the tube by its movement.

I claim:

1. A device for use in monitoring pollution of liquids, comprising:
   means for directing a beam of light having both visible and ultraviolet components through a flowing sample of liquid;
   a pair of photoelectric detectors respectively arranged to detect visible and ultraviolet components of the light from said beam which has been transmitted through said sample and to produce outputs which respectively vary as functions of the detected components;
   means for modulating said beam of light;
   means for demodulating said outputs of said detectors to provide a pair of signals;
   means for deriving from one of said pair of signals a further signal representative of the amplitude of noise components in said one of said pair of signals;
   means for obtaining the difference between respective logarithmically amplified versions of said pair of signals to provide a measure of the organic content of said sample; and
   means for obtaining the difference between respective logarithmically amplified versions of said further signal and said one of said pair of signals to provide a measure of the amount of solid suspended matter in said sample.

2. A device according to claim 1, comprising a dichroic mirror which reflects visible light and transmits ultraviolet light, said mirror being located in the path of the light from said beam which has been transmitted through said sample and said detectors being positioned so as respectively to receive light reflected and transmitted by said mirror.

* * * * *